(12) United States Patent
Sauter

(10) Patent No.: US 11,311,299 B2
(45) Date of Patent: Apr. 26, 2022

(54) SURGICAL CLIP WITH BRACKET-FREE GUIDE SYSTEM

(71) Applicant: Aesculap AG, Tuttlingen (DE)

(72) Inventor: Wolfgang Sauter, Renquishausen (DE)

(73) Assignee: AESCULAP AG, Tuttlingen (DE)

( * ) Notice: Subject to any disclaimer, the term of this patent is extended or adjusted under 35 U.S.C. 154(b) by 0 days.

(21) Appl. No.: 16/765,448

(22) PCT Filed: Nov. 20, 2018

(86) PCT No.: PCT/EP2018/081886
§ 371 (c)(1),
(2) Date: May 19, 2020

(87) PCT Pub. No.: WO2019/097075
PCT Pub. Date: May 23, 2019

(65) Prior Publication Data
US 2020/0275933 A1    Sep. 3, 2020

(30) Foreign Application Priority Data
Nov. 20, 2017  (DE) ...................... 10 2017 127 290.9

(51) Int. Cl.
*A61B 17/12* (2006.01)
*A61B 17/122* (2006.01)
(Continued)

(52) U.S. Cl.
CPC ........ *A61B 17/1227* (2013.01); *A61B 17/128* (2013.01); *A61B 2017/00526* (2013.01)

(58) Field of Classification Search
CPC .............. A61B 17/1227; A61B 17/128; A61B 17/1285; A61B 17/122; A61B 17/105;
(Continued)

(56) References Cited

U.S. PATENT DOCUMENTS 482,323 A    9/1892  Delaney
884,256 A    4/1908  Addie
(Continued)

FOREIGN PATENT DOCUMENTS

CA    2587267 A1    10/2007
CN    1897880 A    1/2007
(Continued)

OTHER PUBLICATIONS

German Search Report Application No. 10 2017 127 290.9, dated Sep. 12, 2018, 16 pages. (with translation).
(Continued)

*Primary Examiner* — Erich G Herbermann
(74) *Attorney, Agent, or Firm* — Culhane Meadows PLLC; Christopher A. Rothe

(57) ABSTRACT

A surgical clip of branch-crossed design has two Z-shaped clip branches connected to each other at a proximal end of each of the clip branches by a spring-elastic connection piece. Each of the clip branches has a jaw part at a distal section with a gripping surface. In an assembled position of the clip, the clip branches cross and the gripping surfaces are opposite each other and are held in contact on one another by a closing force of the spring-elastic connection piece. At least one first clip branch has a groove in which the second clip branch is held and/or guided, at least in sections, such that a displacement of the clip branches in a transverse direction of the clip branches is prevented.

14 Claims, 3 Drawing Sheets

(51) Int. Cl.
*A61B 17/128* (2006.01)
*A61B 17/00* (2006.01)

(58) Field of Classification Search
CPC ............... A61B 17/083; A61B 17/068; A61B 2017/00526; A61B 2017/2825; A61B 2017/2937; A61B 2017/2933; A61B 2017/2927; A61B 2017/07271
See application file for complete search history.

(56) References Cited

U.S. PATENT DOCUMENTS

| | | |
|---|---|---|
| 1,589,076 A | 6/1926 | Haskins |
| 1,758,490 A | 5/1930 | Julius |
| 1,837,277 A | 12/1931 | Lund |
| 2,758,302 A | 8/1956 | White |
| 3,326,217 A | 6/1967 | Kerr |
| 3,598,125 A | 8/1971 | Cogley |
| 3,604,071 A | 9/1971 | Reimels |
| 3,802,437 A | 4/1974 | Kees |
| 3,805,792 A | 4/1974 | Cogley |
| 3,827,438 A | 8/1974 | Kees |
| 3,856,016 A | 12/1974 | Davis |
| 3,954,108 A | 5/1976 | Davis |
| 4,137,919 A | 2/1979 | Farin et al. |
| 4,192,315 A | 3/1980 | Hilzinger et al. |
| 4,324,248 A | 4/1982 | Perlin |
| 4,337,774 A | 7/1982 | Perlin |
| 4,340,061 A | 7/1982 | Kees et al. |
| 4,360,023 A | 11/1982 | Sugita et al. |
| 4,416,266 A | 11/1983 | Baucom |
| 4,444,187 A | 4/1984 | Perlin |
| 4,484,581 A | 11/1984 | Martin et al. |
| 4,569,346 A | 2/1986 | Poirier |
| 4,602,631 A | 7/1986 | Funatsu |
| 4,765,335 A | 8/1988 | Schmidt et al. |
| 4,777,950 A | 10/1988 | Kees |
| 4,796,625 A | 1/1989 | Kees, Jr. |
| 4,835,824 A | 6/1989 | Durham et al. |
| 4,932,955 A | 6/1990 | Merz et al. |
| 4,943,298 A | 7/1990 | Fujita et al. |
| 4,961,743 A * | 10/1990 | Kees, Jr. ............ A61B 17/1227 606/151 |
| 4,966,603 A | 10/1990 | Focelle et al. |
| 4,971,055 A | 11/1990 | Zeppelin |
| 4,983,176 A | 1/1991 | Cushman et al. |
| 5,026,379 A | 6/1991 | Yoon |
| 5,074,870 A | 12/1991 | Zeppelin |
| 5,160,339 A | 11/1992 | Chen et al. |
| 5,171,250 A | 12/1992 | Yoon |
| 5,201,900 A | 4/1993 | Nardella |
| 5,207,692 A | 5/1993 | Kraus et al. |
| 5,217,473 A | 6/1993 | Yoon |
| 5,236,440 A | 8/1993 | Hlavacek |
| 5,312,426 A | 5/1994 | Segawa et al. |
| 5,361,463 A | 11/1994 | Revis |
| 5,366,459 A | 11/1994 | Yoon |
| 5,441,509 A | 8/1995 | Vidal et al. |
| 5,474,569 A | 12/1995 | Zinreich et al. |
| 5,474,732 A | 12/1995 | Korthoff et al. |
| 5,520,701 A | 5/1996 | Lerch |
| D371,390 S | 7/1996 | Johnson |
| 5,609,599 A | 3/1997 | Levin |
| 5,725,763 A | 3/1998 | Bonhomme et al. |
| 5,779,720 A | 7/1998 | Walder-Utz et al. |
| 5,788,716 A | 8/1998 | Kobren et al. |
| D401,626 S | 11/1998 | Shyu |
| 5,924,176 A | 7/1999 | Lee |
| 5,944,729 A | 8/1999 | Blake |
| 6,015,417 A | 1/2000 | Reynolds |
| 6,179,850 B1 * | 1/2001 | Goradia ............ A61B 17/1227 606/158 |
| 6,210,418 B1 | 4/2001 | Storz et al. |
| 6,210,419 B1 | 4/2001 | Mayenberger et al. |
| 6,251,117 B1 | 6/2001 | Kringel et al. |
| 6,428,548 B1 | 8/2002 | Durgin et al. |
| 6,457,218 B1 | 10/2002 | Lawrence |
| 6,537,277 B2 | 3/2003 | Berg et al. |
| 6,776,783 B1 | 8/2004 | Frantzen et al. |
| 7,207,997 B2 | 4/2007 | Shipp et al. |
| 7,572,266 B2 | 8/2009 | Young et al. |
| D600,749 S | 9/2009 | Azman et al. |
| D600,750 S | 9/2009 | Azman et al. |
| 7,678,125 B2 | 3/2010 | Shipp |
| 7,713,284 B2 | 5/2010 | Crofford |
| 7,874,343 B2 | 1/2011 | Hansen |
| 8,706,118 B2 | 4/2014 | Jaiswal et al. |
| 9,289,216 B2 * | 3/2016 | Weisshaupt ........ A61B 17/1227 |
| 9,572,579 B2 | 2/2017 | Weisshaupt |
| 2002/0022844 A1 | 2/2002 | Berg et al. |
| 2002/0111643 A1 | 8/2002 | Herrmann et al. |
| 2002/0117869 A1 | 8/2002 | Wang et al. |
| 2003/0199888 A1 | 10/2003 | Lutze et al. |
| 2004/0092961 A1 | 5/2004 | Viola |
| 2004/0147942 A1 | 7/2004 | Chao |
| 2006/0195125 A1 | 8/2006 | Sakakine et al. |
| 2006/0212049 A1 | 9/2006 | Mohiuddin |
| 2006/0235445 A1 | 10/2006 | Birk et al. |
| 2007/0112365 A1 | 5/2007 | Hilal et al. |
| 2007/0191883 A1 | 8/2007 | Lazic et al. |
| 2008/0077144 A1 | 3/2008 | Crofford |
| 2008/0147092 A1 | 6/2008 | Rogge et al. |
| 2008/0312670 A1 | 12/2008 | Lutze et al. |
| 2009/0240266 A1 | 9/2009 | Dennis |
| 2010/0036398 A1 | 2/2010 | Aboud |
| 2011/0152887 A1 | 6/2011 | Surti et al. |
| 2011/0224701 A1 | 9/2011 | Menn |
| 2011/0288571 A1 | 11/2011 | Steinhilper et al. |
| 2012/0184976 A1 * | 7/2012 | Nakamura ........... A61B 17/122 606/158 |
| 2013/0172914 A1 | 7/2013 | Weisshaupt |
| 2013/0184726 A1 | 7/2013 | Weisshaupt et al. |
| 2014/0114332 A1 * | 4/2014 | Lutze ................... A61B 17/083 606/151 |
| 2014/0194908 A1 | 7/2014 | Lazic |
| 2015/0008629 A1 | 1/2015 | Kuno et al. |
| 2015/0057684 A1 | 2/2015 | Zieris |
| 2015/0164510 A1 * | 6/2015 | Pleil .................. A61B 17/1227 606/157 |
| 2015/0308033 A1 | 10/2015 | Boocock |
| 2016/0157867 A1 | 6/2016 | Zieris et al. |
| 2017/0296195 A1 | 10/2017 | Pleil et al. |

FOREIGN PATENT DOCUMENTS

| | | |
|---|---|---|
| CN | 103153213 A | 6/2013 |
| CN | 204581368 U | 8/2015 |
| DE | 2036725 A1 | 2/1971 |
| DE | 2647018 A1 | 5/1977 |
| DE | 2639956 A1 | 3/1978 |
| DE | 2658478 B1 | 4/1978 |
| DE | 2952618 A1 | 7/1981 |
| DE | 3139488 A1 | 4/1983 |
| DE | 3419928 A1 | 4/1985 |
| DE | 3523031 A1 | 1/1986 |
| DE | 3722311 A1 | 1/1989 |
| DE | 8911948 U1 | 12/1989 |
| DE | 4000086 A1 | 7/1990 |
| DE | 4319829 C1 | 4/1994 |
| DE | 29604518 U1 | 5/1996 |
| DE | 19520158 A1 | 12/1996 |
| DE | 69028200 T2 | 2/1997 |
| DE | 3723167 C2 | 4/1997 |
| DE | 29706218 U1 | 7/1997 |
| DE | 19737976 A1 | 3/1999 |
| DE | 19809121 C1 | 8/1999 |
| DE | 19827093 A1 | 1/2000 |
| DE | 19858580 C1 | 9/2000 |
| DE | 19907354 A1 | 9/2000 |
| DE | 20107378 U1 | 8/2001 |
| DE | 20303496 U1 | 7/2003 |
| DE | 10309491 A1 | 9/2004 |
| DE | 102004016859 A1 | 10/2005 |
| DE | 202006000329 U1 | 3/2006 |

(56) References Cited

FOREIGN PATENT DOCUMENTS

| | | |
|---|---|---|
| DE | 202006002436 U1 | 6/2006 |
| DE | 202006010414 U1 | 9/2006 |
| DE | 102006001344 A1 | 7/2007 |
| DE | 102006031092 B3 | 1/2008 |
| DE | 202010008512 U1 | 12/2010 |
| DE | 202010008714 U1 | 1/2011 |
| DE | 202011051881 U1 | 11/2011 |
| DE | 102011055094 A1 | 5/2013 |
| DE | 102013107876 A1 | 1/2015 |
| DE | 102014114946 A1 | 4/2016 |
| EP | 0105414 A1 | 4/1984 |
| EP | 0122046 A1 | 10/1984 |
| EP | 0346084 A1 | 12/1989 |
| EP | 0567965 A3 | 6/1994 |
| EP | 1196094 B1 | 1/2003 |
| EP | 2589346 A1 | 5/2013 |
| EP | 2752164 A1 | 7/2014 |
| GB | 1557682 A | 12/1979 |
| GB | 2161206 A | 1/1986 |
| JP | S56124807 A | 2/1986 |
| JP | S6182426 U | 5/1986 |
| JP | H01310654 A | 12/1989 |
| JP | H06007360 A | 1/1994 |
| JP | 2003102736 A | 4/2003 |
| JP | 2006519674 A | 8/2006 |
| JP | 2009523044 A | 6/2009 |
| JP | 3157486 U | 2/2010 |
| JP | 5314064 B2 | 10/2013 |
| JP | 2015516218 A | 6/2015 |
| KR | 20150070866 A | 6/2015 |
| RU | 2102017 C1 | 1/1998 |
| RU | 2009112889 A | 10/2010 |
| WO | 9818389 A1 | 5/1998 |
| WO | 9944511 | 9/1999 |
| WO | 0135832 A2 | 5/2001 |
| WO | 2004080275 A2 | 9/2004 |
| WO | 2007006140 A1 | 1/2007 |
| WO | 2011068073 A1 | 6/2011 |
| WO | 2012031949 A1 | 3/2012 |
| WO | 2012045500 A1 | 4/2012 |
| WO | 2013111416 A1 | 8/2013 |
| WO | 2013160452 A1 | 10/2013 |
| WO | 2014001008 A1 | 1/2014 |
| WO | 2014012718 A1 | 1/2014 |
| WO | 2016058988 A1 | 4/2016 |

OTHER PUBLICATIONS

International Search Report Application No. PCT/EP2018/081886, dated Feb. 27, 2019, 9 pages. (with translation).
Office Action received in Chinese Application No. 201780025620.2 dated Nov. 3, 2020, with translation, 12 pages.
Written Opinion received in International Application No. PCT/EP2014/064610 dated Oct. 13, 2014,with translation, 12 pages.
Office Action received in Chinese Application No. 201780025620.2 dated May 10, 2021, with translation, 16 pages.
Search Report received in International Application No. PCT/EP2014/064610 dated Oct. 13, 2014, with translation, 6 pages.
Search Report and Written Opinion received in International Application No. PCT/EP2013/058738, dated Aug. 29, 2013, with translation, 17 pages.
Search Report and Written Opinion received in International Application No. PCT/EP2017/059292, dated Jul. 18, 2017, with translation, 21 pages.
Search Report received in Germany Application No. 10 2016 107 587.6, dated Feb. 3, 2017 with translation, 13 pages.
Search Report received in International Application No. PCT/EP2013/060924 dated Oct. 8, 2013, with translation, 6 pages.

* cited by examiner

SURGICAL CLIP WITH BRACKET-FREE GUIDE SYSTEM

CROSS-REFERENCE TO RELATED APPLICATION(S)

This is the United States national phase entry of International Application No. PCT/EP2018/081886, filed Nov. 20, 2018, which claims the benefit of priority of German Application No. 10 2017 127 290.9, filed Nov. 20, 2017. The contents of International Application No. PCT/EP2018/081886 and German Application No. 10 2017 127 290.9 are incorporated by reference herein in their entireties.

FIELD

The invention relates to a surgical clip, in particular an aneurysm clip, for clamping or pinching off vessels.

BACKGROUND

For the treatment of aneurysms, surgical clips, also known as aneurysm clips, are used, which are surgically inserted and remain in the patient's body. By 'clipping' cerebral vessels, vascular bulges can be cut off from the rest of the bloodstream so that blood can no longer flow into the aneurysm. For this purpose, the surgical clip is placed on the neck of an aneurysm during the surgery and, in a permanent closed position, blocks the blood supply to the vascular bulge like a clamp. This prevents the vascular bulge from bursting and the aneurysm can heal.

A surgical clip usually has two branches or jaw parts, which are connected at their proximal end by a connection piece, usually in the form of a spring-elastic portion or element. Proximal in the sense of the patent application is defined as the end facing the user or the end directed towards the user, distal is defined as the end facing away from the user or the end directed away from the user. The jaw parts are pre-tensioned against each other by the spring-elastic portion or element when the clip is in the inserted state and clamp the neck of the vessel between their gripping surfaces. Surgical clips of the branch-crossed design are known from the prior art, which are manufactured integrally in one piece (material) from one wire. For this purpose, first of all the longitudinal portions of the (unbent) wire are formed into the required shape, e.g. gripping surfaces are provided/designed and/or a special cross-section of the wire is formed/shaped at certain points. Subsequently, the wire is bent into the manufacturing position. In a clip of this type, the two branches have an S-shaped or Z-shaped form and are connected to each other at their proximal ends by a wire coil, which as a "double loop" assumes the function of a leg spring as a spring-elastic connection element. In the manufacturing position, the Z-shaped branches do not cross each other and their distal ends point away from the central axis of the clip. Gripping surfaces are arranged on the distal portions of the Z shape, which face outwards in the manufacturing position, i.e. away from the central axis of the clip.

By applying force, the clip is transferred from the manufacturing position to the mounting position. In the mounting position, the branches cross each other in the area of the center portions of the Z shape. The branches are bent or shaped in such a way that the gripping surfaces are opposite each other in the mounting position and are supported or rest against each other against the spring force of the leg spring. The gripping surfaces are held against each other by the pre-tensioning force of the leg spring. This corresponds to the closed position of the clip. In order to open the clip, the gripping surfaces are pushed apart crosswise. When released, the branches spring back into the closed position.

In order to prevent the branches from slipping in the transverse direction of the gripping surfaces, the branches are guided on one or both sides according to the prior art. In the case of one-sided guidance, the branches lie against each other in the crossed area of the center portions, so that movement of the branches towards each other in the transverse direction is limited. However, movement of the branches away from each other in the transverse direction is not limited.

For this reason, a box lock is created in the prior art for the double-sided guidance, which is produced in the form of a securing bracket or securing plate, for example. In the mounting position of the clip, a securing element, e.g. a wire bracket or plate, is attached to the crossed area in such a way that the securing element limits the movement of the branches away from each other in the transverse direction and the branches are thus guided on both sides during the opening and closing movement.

Usually, the securing element is welded to the clip. However, the manufacturing process, which involves the steps of forming, bending and then attaching an additional securing element to the clip, in particular by welding, has considerable disadvantages. The welding process causes considerable lateral distortion and also requires a high degree of straightening and finishing in further production steps. This leads to increased costs and variable quality of the produced clip.

It is known that in surgical instruments of the scissor type, in which the branches are rotatably connected to each other between their ends, slipping of the branches in the transverse direction is prevented by a flap closure or double flap closure. However, a flap closure only provides protection against slipping of the branches up to an opening angle at which the opening distance of the branches to each other does not exceed the height of the flaps. The flaps are therefore arranged close to the pivot point where the distance between the inner surfaces of the branches to each other is minimal. For surgical clips of the branch-crossed design ('alpha design'), in which the branches are connected to each other at their ends and in which, when the clip is open for insertion, the practically required distance of the branches from each other far exceeds the normal flap height even at its smallest point, a flap closure is unsuitable.

SUMMARY

It is therefore the object of the invention to eliminate or at least reduce the disadvantages of the prior art. In particular, the manufacture of a surgical clip, including securing against slippage of the branches in the transverse direction, is intended to increase the quality and reduce the time and financial expenditure, in particular by providing a clip with an integral securing portion made of a single piece of material.

A basic idea of the invention is to manufacture a surgical clip including a securing mechanism for securing the closing area of the clip branches without an additional, separate component.

In concrete terms, the object is solved by a surgical clip of the branch-crossed design, in particular an aneurysm clip, with two Z-shaped or S-shaped clip branches, each of which has a proximal portion, a Z-shaped or S-shaped center portion and a distal portion, which are furthermore connected at one proximal end of each of the clip branches via a spring-elastic connection piece or pretensioning element, for example in the form of a leg spring, (integrally made of a single piece of material) and each have a jaw part with a (profiled) gripping surface on a distal portion of the clip branches, wherein in a (metastable) mounting position of the clip, the clip branches are crossed over (at their center portions, preferably adjacent to one another), the gripping surfaces are opposite each other, preferably substantially flush, and these are held adjacent to each other by a closing force of the spring-elastic connection piece. At least one first clip branch (in its S-shaped or Z-shaped center portion) has a (longitudinal) groove (only) open towards the opposite clip branch, in which (at the groove bottom) the second clip branch is held (supported) and/or guided at least in sections (in its center portion) in such a way (longitudinally movable/movable) that a displacement of the clip branches in a transverse direction of the clip branches, in particular transverse direction of the gripping surfaces, is prevented. Preferably, both clip branches each have a (longitudinal) groove open towards the opposite clip branch, in which (at the groove bottom of which) the respective other clip branch is held (supported) and/or guided at least in sections (longitudinally movable/movable).

The proximal portions and/or the distal portions of the clip branches preferably run linear/straight in the longitudinal direction of the clip/the clip branches. Preferably, the groove is located at the distal end of the center portion and/or the groove bottom forms the distal end of the center portions.

The clip branches are thus secured against slipping in a transverse direction of the clip branches or gripping surfaces relative to each other by the at least one groove or its groove flanks when assuming the (metastable) mounting position starting from a defined degree of closure, when leaving the (metastable) mounting position up to a defined degree of opening, and when remaining in the (metastable) mounting position. In particular, the securing mechanism can be milled into the clip in the form of the open (longitudinal) groove.

Up to now, the arrangement of a so-called penetrating/push-through box, for example, has been known to secure the clip branches against relative transverse slippage/displacement. According to this, a box-shaped or eyelet-shaped opening/pass-through is formed in the central portion of a branch of a clip of the crossed branch type, through which the other branch is passed. The manufacture or assembly of such a clip is difficult and complex.

In the present invention, however, at least one clip branch is formed in its Z-shaped or S-shaped center portion on the side facing the other clip branch with the longitudinal groove which, because it is arranged in the Z-shaped or S-shaped center portion, extends obliquely to the longitudinal axis of the clip. If the other clip branch is now also inserted into the groove in the area of its Z-shaped or S-shaped center portion (i.e. in its area extending obliquely to the longitudinal direction of the clip), this results in a kind of groove-spring guide, whereby the Z-shaped or S-shaped portion of the other clip branch is slidingly guided in the groove of one clip branch obliquely to the (longitudinal) axis of the clip. The oblique orientation in this area is such that, in the event of a relative movement of the two clip branches away from or towards each other, the other clip branch remains slidingly guided in the groove of one clip branch, whereby lateral slipping of the two clip branches is prevented by the groove flanks. Furthermore, inserting the other clip branch into the groove of the one clip branch is easily possible.

It should be noted that the clip, when it is not under the influence of external force, can basically assume two positions. In the manufacturing position of the clip in which it is produced, the clip branches are not yet crossed. By applying external force to the clip branches, they are then brought into a crossed position, in particular the central, Z-shaped or S-shaped portions of the clip branches are crossed and at least the other clip branch is inserted into the at least one groove of one clip branch.

In this context, the (metastable) mounting position of the clip means the state or position of the clip after crossing the clip branches, in which the gripping surfaces are held (in a form-fit and/or force-fit) against each other, while the clip is no longer under the influence of external force. It can also be said that the gripping surfaces rest on each other in the mounting position of the clip, while the clip branches are pretensioned against each other by the pretensioning force of the spring-elastic, proximal connection piece.

Furthermore, a proximal end or portion is always understood to be an end or portion facing the user (surgeon) or facing away from the patient and, correspondingly, a distal end or portion is always understood to be an end or portion facing away from the user or facing the patient (patient tissue surgery section).

In other words, the two gripping surfaces at the clip branches are positioned one above the other in a (metastable) mounting position of the clip (essentially in a flush manner) and pressed against each other by the pretensioning force of the spring-elastic connection piece. In this way, a clamping effect is created between the gripping surfaces. The relative position of the gripping surfaces in their transverse direction, or the corresponding relative position of the clip branches, is secured by the securing mechanism in the form of the groove-spring connection of the two clip branches with each other, so that the gripping surfaces are located one above the other when the clip is in the (metastable) mounting position, assumes this position when the clip is closed and/or leaves it again when it is opened. The securing mechanism is an integral (one-piece) component of the clip, i.e. the clip, including the securing mechanism, is formed or manufactured from a single component. The securing of the clip branches in the transverse direction of the gripping surfaces is therefore accomplished without an additional, separate component.

Advantageously, this makes the time-consuming step of welding or otherwise attaching, e.g. an end plate or end bracket, to the clip, including the subsequent post-processing steps, obsolete. The elimination of the manual processing step, such as welding, also offers the possibility of automating in the production of the clip. Variations in quality can also be avoided or reduced. Overall, the manufacturing costs can be reduced and the quality of the end product can be increased.

In particular, the grooves of the first clip branch and the second clip branch can move along each other like rails, or the clip branches are guided along each other like rails. At least the second clip branch can have a portion (rail, strip, spring) corresponding to the groove of the first clip branch, this portion being held and/or slidingly guided in the groove or on which the groove is positioned and/or slides along. Preferably, the second clip branch also has a groove in which a corresponding portion at the first clip branch is equally held and/or slidably guided. The complete range of movement of the clip branches can be determined by a corresponding concrete design of the rail shape and its arrangement on the clip.

Preferably, the center portion of the (respective) clip branch, at least in sections or completely, can be guided and/or is held in the groove, e.g. a longitudinal groove, of the other clip branch. This is particularly advantageous if both clip branches have a groove for guiding the other clip branch. Since the center portions are crossed over in the mounting position, guiding of the center portion of one clip branch allows the two clip branches to guide each other through the respective grooves simultaneously or to hold them together. The clip branches can thus be guided or held together along a center portion/the center portions during the opening and/or closing movement of the clip up to a defined opening angle or from a defined closing angle.

Preferably, a side wall of the groove/groove flank is formed in the form of a protrusion, in particular a flap, which faces the other clip branch, in particular its center portion. In particular, the protrusion can be arranged at the distal end of the center portion and can be oriented in such a way that it is directed away from the proximal end of the distal portion (in the longitudinal direction of the clip/the clip branch or obliquely to the longitudinal direction of the clip/the clip branch). It can also be said that the protrusion can be arranged at or in the area of the proximal end of the distal portion of at least one clip branch, preferably both clip branches, so that the groove faces the (crossing) center portion of the respective other clip branch. In particular, the protrusion is formed integrally with the clip branch in one piece, and the groove is especially preferably created by milling. The proximal end of the distal portion of the clip branch is easily accessible due to the Z-shape or S-shape of the clip branches, so that this position can be used advantageously during manufacture, for example during milling.

In addition, the groove is preferably arranged (respectively) eccentrically at the clip branch, in particular, the groove lies completely in one half of the branch in the transverse direction of the clip branch. Especially preferably, the groove borders on the central or longitudinal axis of the clip branch. The arrangement of the groove completely in one half of the branch is particularly advantageous if both clip branches have a groove for guiding/holding the respective other clip branch. Only then is it possible for the gripping surfaces or distal portions to lie (flushly) against each other in the mounting position, when the two clip branches have the same shape.

Especially preferably, the center portion of one or both clip branches has a recess/material removal in the function of a guide path, which is intended and adapted to guide and/or accommodate the protrusion located at the (respective) other clip branch. The recess can follow the Z-shaped course of the center portion in such a way that a guide ridge is formed on an upper side of the center portion. In particular, the recess is milled into a side surface of the center portion. The term side surfaces refers to the surfaces of a clip branch that are orthogonal to the gripping surface.

Lateral removal of the material (on one side surface of the clip branch) in the area of the desired recess at the center portion advantageously reduces the material thickness or strength or width of the center portion, so that the corresponding groove on the other clip branch can also take up a smaller width or does not have to be widened to cover the area of the center portion that has been reduced by removal.

Especially preferably, the proximal portions of the clip branches in the transverse direction and/or longitudinal direction of the clip branches lie at least partially, ideally completely, opposite each other or overlap at least partially, ideally completely, at one height to each other. Advantageously, this prevents the clip branches or gripping surfaces from being pretensioned in their transverse direction to each other in the (metastable) mounting position and the securing mechanism is therefore not loaded or only slightly loaded.

Preferably, the center portion of at least the second clip branch, preferably of both clip branches, is about half as wide as the proximal portion and the distal portion. In this way, the center portions of the two clip branches can be joined together so that the clip is no wider in the area of the center portions than in areas of the distal portions and proximal portions.

For this purpose (in the mounting position of the clip), the side surface portions of the proximal portion, of the center portion and of the distal portion can be arranged in alignment, in particular on the side surface of a clip branch which (in the area of the center portion) faces away from the respective other clip branch and/or represents an outer side of the clip, while on the side surface of the clip branch facing the other clip branch (in the area of the center portion), the side surface portion of the center portion is cut back from the side surface portions of the proximal portion and distal portion by approximately half the width of the proximal portion and distal portion.

As a general advantage, the milling manufacturing process offers good automation possibilities and is associated with small deviations in the workpiece quality, which can have an advantageous effect on the manufacturing costs.

In summary, according to the present invention, the surgical clip/aneurysm clip may have two clip branches/jaw parts which are joined at their proximal ends by the leg spring integrally in one piece of material. Both clip branches can each have an S-shaped or Z-shaped loop/curvature at their center portions in such a way that the two clip branches can (freely) cross over each other in these center portions. In order to still be able to guarantee guidance of the two clip branches, or to prevent the clip branches from being spaced apart in the transverse direction to the longitudinal axis of the branch (e.g. in the case of an external transverse force application), at least one of the two clip branches can have an open longitudinal groove in its S-shaped or Z-shaped curved center portion, which faces the other clip branch or the S-shaped or Z-shaped curved center portion in a crossed state and in which the other clip branch or its S-shaped or Z-shaped curved center portion can be slidingly guided.

This allows the clip to be easily transferred from a non-crossed manufacturing position to a crossed mounting position by inserting one clip branch in its S-shaped or Z-curved center portion into the open groove in the S-shaped or Z-curved center portion of the other clip branch, creating lateral guidance in the transverse direction of the branch. On the other hand, this also enables lateral guidance when (partially) opening the clip from the mounting position and when closing or re-entering the mounting position.

BRIEF DESCRIPTION OF THE DRAWING FIGURES

The invention is further described hereinafter by means of a preferred embodiment with reference to the attached drawing figures, of which:

The figures are merely schematic in nature and serve exclusively to understand the invention. The same elements are designated by the same reference signs.

DETAILED DESCRIPTION

Figure 1:
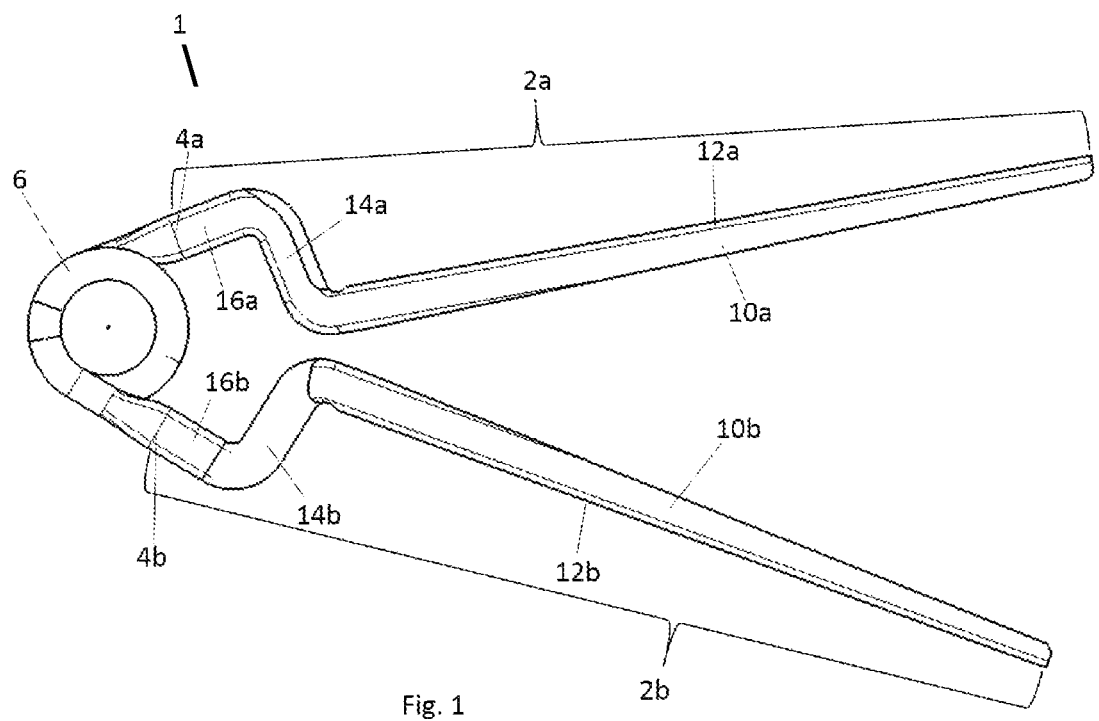
FIG. 1 shows a side view of a surgical clip in a configuration example of the invention in the manufacturing position.

FIG. 1 shows a surgical clip 1 in a configuration example of the invention with two Z-shaped or S-shaped clip branches 2a, 2b, which are connected to each other at one proximal end 4a, 4b of the clip branches 2a, 2b via a connection piece 6. The connection piece 6 is a leg spring in this embodiment. The clip branches 2a, 2b each have a linear distal portion 8a, 8b, on which jaw parts 10a, 10b with profiled gripping surfaces 12a, 12b are arranged, a Z-shaped or S-shaped center portion 14a, 14b and a linear proximal portion 16a, 16b. In the manufacturing position of clip 1, the gripping surfaces 12a, 12b are directed or facing away from each other.

When external force is applied to the clip branches 2a, 2b both in the closing direction and in the transverse direction of the clip branches 2a, 2b (in which the clip branches 2a, 2b are pressed away from each other), the clip 1 leaves the manufacturing position and the clip branches 2a, 2b are crossed over in such a way that the gripping surfaces 12a, 12b now face each other, and the center portions 14a, 14b cross over each other. The center portions 14a, 14b have a smaller cross-section (not shown in FIG. 1) than the distal and proximal portions 8a, 8b, 16a, 16b. When the external force is released, the center portions 14a, 14b slide along each other in the crossed area and the gripping surfaces 12a, 12b move towards each other until they come into contact due to their (almost) parallel orientation. The clip 1 has thus assumed the mounting position described hereinafter.

Figure 2:
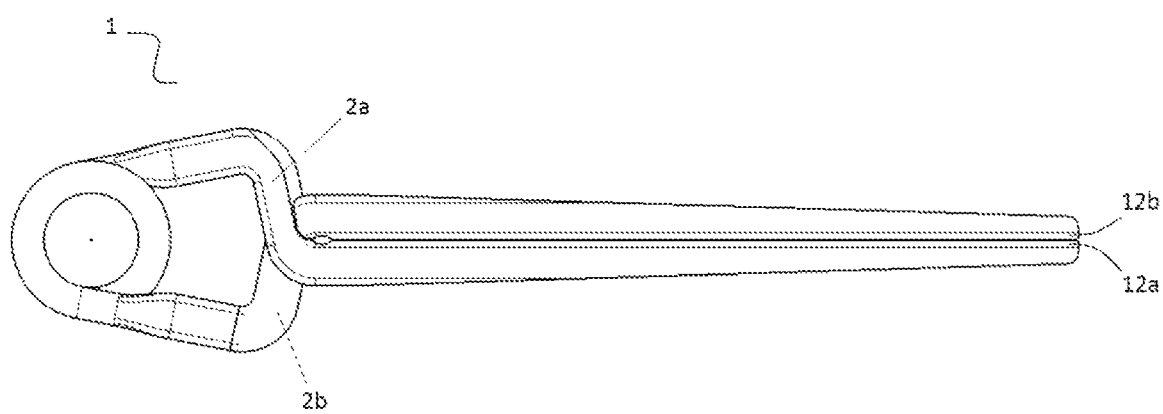
FIG. 2 shows a side view of the surgical clip from FIG. 1 in the mounting position.

FIG. 2 shows the mounting position of the clip 1 of FIG. 1. In the mounting position, the center portions 14a, 14b of the clip branches 2a, 2b are crossed and the gripping surfaces 12a, 12b of the distal portion 8a, 8b are facing each other and abutting each other. The gripping surfaces 12a, 12b are ideally flush with each other in their transverse direction. The pretensioning of the leg spring exerts a force on the clip branches 2a, 2b in the closing direction of the jaw parts 10a, 10b, which keeps the gripping surfaces 12a, 12b lying on top of each other. The form-fit and/or friction-fit contact of the gripping surfaces 12a, 12b and the pretensioning of the clip branches 2a, 2b by the leg spring thus creates a clamping effect between the gripping surfaces 12a, 12b.

Figure 3:
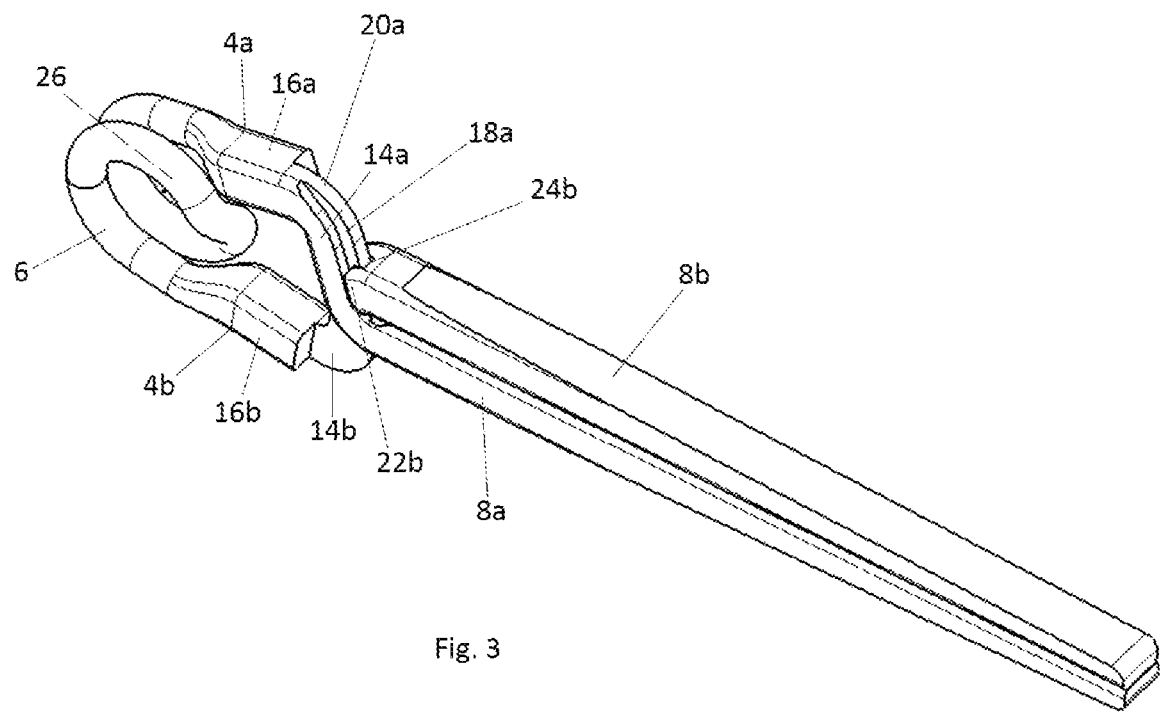
FIG. 3 shows a perspective view of the surgical clip from FIG. 1 in the mounting position.

FIG. 3 shows a perspective view of the surgical clip from FIG. 1 in the mounting position. The first clip branch 2a is in the area of the center portion 14a (approximately) half as wide as in the distal and proximal portions 8a, 16a. On the side of the clip branch 2a facing away from the crossing center portion 14b of the second clip branch 2b, the side surfaces of the proximal, center and distal portions 16a, 14a, 8a are arranged/oriented in a flush or aligned manner, while on the other side of the clip branch 2a, the side surface of the center portion 14a is cut back to (approximately) half the width (in the transverse direction of the branch) of the distal and proximal portions 8a, 16a (i.e. to their center). Milling, for example, can be used to create a cut back. On the side surface facing away from the intersecting center portion 14b, the center portion 14a has a recess or guide path 18a that follows the Z-shaped or S-shaped course of the center portion in such a way that a guide ridge or guide web 20a is created on the top side of the clip branch 2a in the area of the center portion, which is narrower than the total width of the center portion 14a (in the transverse direction of the clip branch 2a). The top side of a clip branch 2a, 2b is the side on which the gripping surface 12a, 12b is arranged.

The second clip branch 2b has a flap-shaped protrusion 22b on the side facing the intersecting center portion 14a, at the proximal end of its distal portion 8b or at the distal end of the center portion 14b. The protrusion 22b forms a groove flank/side wall of a groove 24b, whereby the groove 24b faces the guide ridge 20a of the first clip branch 2a, i.e. is open in the direction of the guide ridge 20a. The proximal end of the distal portion 8b (the transverse branch surface at the proximal end) or the distal end of the center portion 14b (the transverse branch surface at the distal end) forms the groove bottom. The groove 24b embraces the guide ridge 20a, preferably in a complementary manner, whereby the protrusion 22b is accommodated in the guide path 18a and/or is guided along the guide path 18a in a rail-like manner or slides along it when opening and/or closing the clip 1. This prevents a movement of the clip branches 2a, 2b in the transverse direction. More precisely, the crossed area of the center portions 14a, 14b limits the transverse movement of the clip branches 2a, 2b towards each other and the protrusion 22b limits the transverse movement of the clip branches 2a, 2b away from each other.

Furthermore, FIG. 3 shows that the distal portions 8a, 8b as well as the proximal portions 16a, 16b are essentially completely opposite each other in the transverse direction and longitudinal direction of the clip branches 2a, 2b, but at least in the transverse direction. The center portions 14a, 14b are arranged next to each other or behind each other in the transverse direction. Here, the cut-back of the side surfaces of the center portions 14a, 14b facing each other by half the width of the distal and proximal portions 8a, 8b, 16a, 16b comes into play. The loop 26 of the leg spring is angled or curved in such a way that the side surfaces of the proximal portions 16a, 16b on both sides are essentially aligned with each other.

It should also be noted that the clip branches 2a, 2b are designed in the same form and interlock in the same way.

Figure 4:
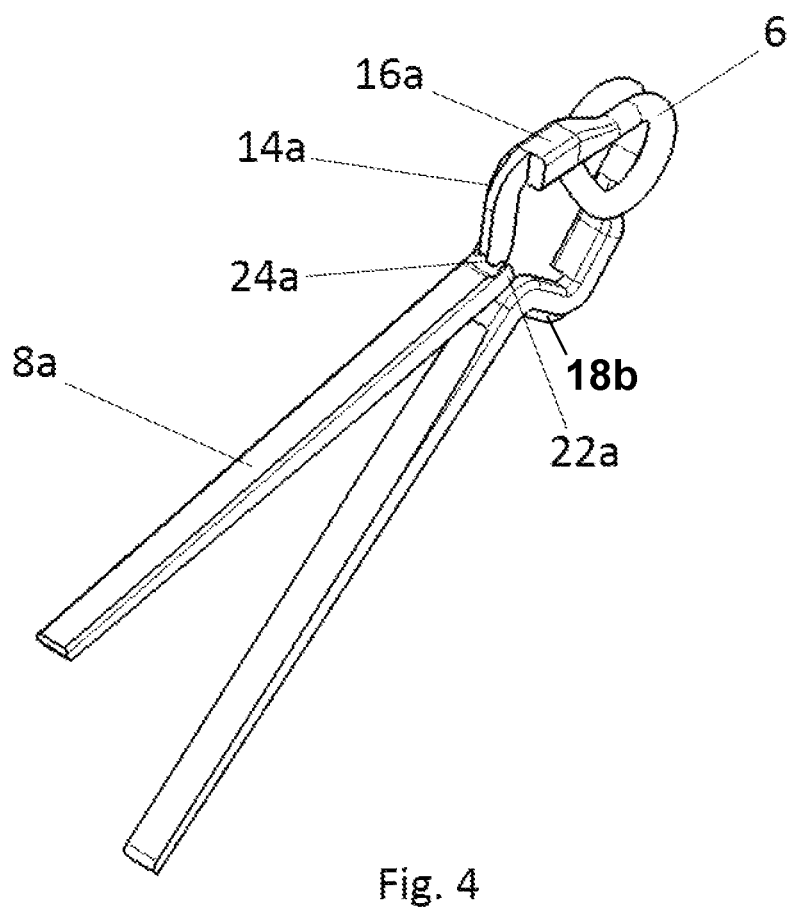
FIG. 4 shows a perspective view of the surgical clip from FIG. 1 in the manufacturing position.

FIG. 4 shows a perspective view of the surgical clip 1 from FIG. 1 in the manufacturing position. In this state, the clip branches 2a, 2b are not yet crossed. Before use, the clip 1 is transferred to the mounting position.

Figure 5:
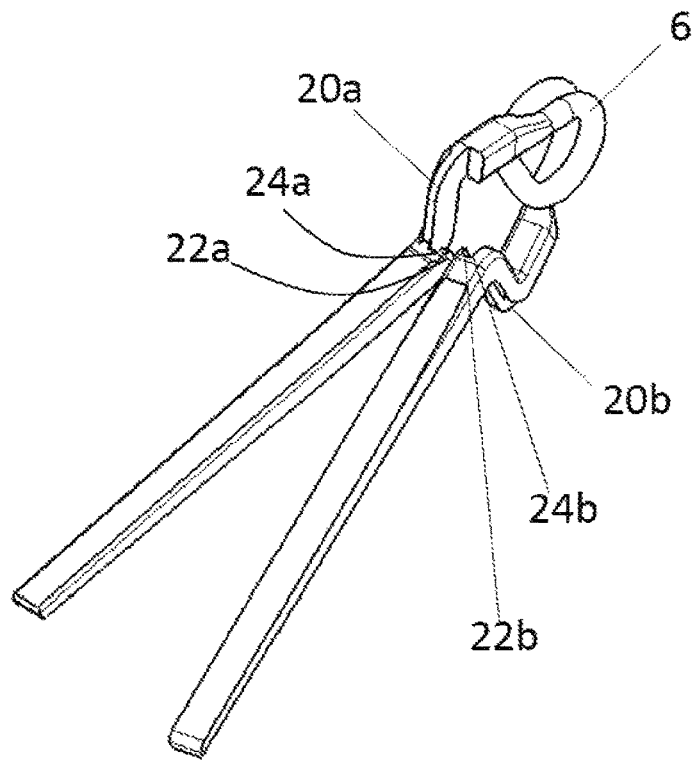
FIG. 5 shows a perspective view of the surgical clip from FIG. 1 in a transitional position.

FIG. 5 shows a perspective view of the surgical clip 1 from FIG. 1 in a transition position during the transfer from the manufacturing position to the mounting position. Under external force applied to the clip branches 2a, 2b, for example with application pliers (not shown), the clip branches 2a, 2b are pressed apart in the transverse direction as described above. In the position of the clip 1 shown in FIG. 5, the distal portions 8a, 8b lie next to each other before they are passed in the opening/closing direction of the jaw parts 10a, 10b under (increasing) external force on the clip branches 2a, 2b so that the clip branches 2a, 2b cross over each other at the center portions 14a, 14b. While the distal portions 8a, 8b lie next to each other, the clip branches 2a, 2b are under tension against the pretensioning force of the leg spring in the opening/closing direction of the jaw parts 10a, 10b as well as in the transverse direction of the clip branches 2a, 2b.

Figure 6:
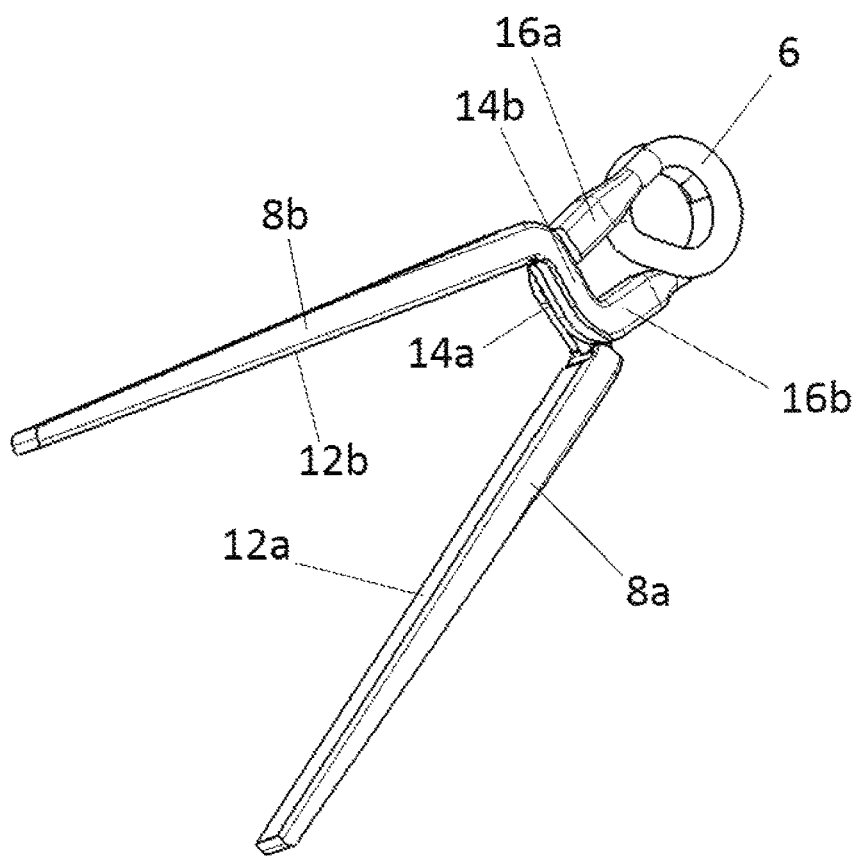
FIG. 6 shows a perspective view of the surgical clip from FIG. 1 in the critical opening state.

FIG. 6 shows a perspective view of the surgical clip 1 from FIG. 1 in a critical opening state, in which the grooves 24a, 24b can be placed on and/or detached from the corresponding guide ridge 20a, 20b. It can also be said that the clip 1 can be hooked in and/or unhooked in this position. In order to bring (hook in) the clip 1 from the manufacturing position into the mounting position, the clip branches 2a, 2b are brought into a critical opening angle under external force, in which the projections 22a, 22b are located in front of the corresponding guide paths 18a, 18b in the closing direction of the jaw parts 10a, 10b. In this state, the facing side surfaces of the center portions 14a, 14b lie against each other and the projections 22a, 22b slide along the guide paths 18a, 18b when the external force in the closing direction of the jaw parts 10a, 10b decreases until the gripping surfaces 12a, 12b lie against each other and the clip 1 assumes its mounting position. While the projections 22a, 22b slide along the guide paths 18a, 18b, the grooves 24a, 24b embrace the guide ridge 20a, 20b and secure the clip branches 2a, 2b against slipping in the transverse direction. In the same way, the clip 1 can be unhooked when the critical opening state is reached or exceeded and can be transferred back to its manufacturing position.

Unintentional exceeding of the critical opening state, in which the clip 1 is unhooked, can be prevented by using suitable application pliers. For example, it is possible to block the opening movement of the clip branches 2a, 2b in a form-fitting manner by a plier section when a critical opening angle is reached or before the critical opening angle is reached.

In the entire area of the groove-guide ridge engagement, i.e. in all positions of the clip branches 2a, 2b in relation to each other in which the grooves 24a, 24b embrace the guide ridge 26a, 26b, the clip branches 2a, 2b are secured against displacement in the transverse direction to each other. By exceeding the critical opening condition, the guidance of the grooves 24a, 24b of the clip branches 2a, 2b can be unhooked or, in a position in which the opening angle is larger than the critical opening angle, the guidance of the grooves 24a, 24b can be hooked and/or unhooked.

The invention claimed is:

1. A surgical clip of a branch-crossed design with a first clip branch and a second clip branch, respective center portions in a longitudinal direction of which each extend in a Z shape, which are connected to each other at respective proximal ends of the clip branches via a spring-elastic connection piece, and have, at respective distal portions of the clip branches, a jaw part with a gripping surface, wherein in a mounting position of the clip, the clip branches are crossed over, the gripping surfaces lie opposite each other, and are held lying against each other via a closing force of the spring-elastic connection piece,
wherein at least the first clip branch has a longitudinal groove in its center portion, the longitudinal groove extending in a Z-shaped manner and open only towards the second clip branch, in which the second clip branch is supported and/or guided in its center portion extending in a Z-shaped manner, at least in sections of the second clip branch, in such a way that a relative movement of the clip branches in an opening/closing direction along the longitudinal groove is possible, but a displacement of the clip branches in a direction transverse to the opening/closing direction is prevented,
wherein a first side wall or a first flank of the longitudinal groove is a protrusion with an end face facing the second clip branch in the longitudinal direction so that the longitudinal groove is an open longitudinal groove, and a second side wall or a second flank of the longitudinal groove is formed by the center portion of the first clip branch,
wherein the center portion of the second clip branch has a recess which is provided and adapted to guide and/or receive the protrusion arranged at the first clip branch,
wherein the recess follows a Z-shaped course of the center portion of the second clip branch in such a way that a guide ridge is formed on an upper side of the center portion of the second clip branch, and
wherein the guide ridge extends along the longitudinal direction, and the recess has a dimension corresponding to a dimension of the protrusion so that a height of the guide ridge corresponds to the length of the protrusion.

2. The surgical clip according to claim 1, wherein the center portion of the second clip branch is guided and/or held in the longitudinal groove of the first clip branch.

3. The surgical clip according to claim 1, wherein the first clip branch and the second clip branch each have a longitudinal groove in their center portions in which the center portion of the respective other clip branch is guided.

4. The surgical clip according to claim 1, wherein the protrusion is formed integrally with the first clip branch as one piece of material.

5. The surgical clip according to claim 1, wherein the longitudinal groove is arranged eccentrically on the first clip branch.

6. The surgical clip according to claim 1, wherein proximal portions of the clip branches are at least partially opposite each other in a transverse direction of the clip branches.

7. The surgical clip according to claim 1, wherein the center portion of at least the second clip branch is about half as wide as a proximal portion of the second clip branch and about half as wide as a distal portion of the second clip branch.

8. The surgical clip according to claim 7, wherein, on a side surface of the second clip branch facing away from the first clip branch, side surfaces of the proximal portion of the second clip branch, of the center portion of the second clip branch, and of the distal portion of the second clip branch are arranged in alignment, while on a side surface of the second clip branch facing the first clip branch, the side surface facing the first clip branch is cut back relative to the side surfaces of the proximal and distal portions of the second clip branch by approximately half the width of the proximal and distal portions of the second clip branch.

9. The surgical clip according to claim 1, wherein the first side wall or the first flank of the longitudinal groove has a plane surface facing towards the second side wall or the second groove flank in the direction transverse to the opening/closing direction.

10. The surgical clip according to claim 1, wherein the surgical clip is formed integrally as one piece of material.

11. The surgical clip according to claim 1, wherein the first clip branch is identical in form to the second clip branch and is opposite to the second clip branch according to the branch crossed design.

12. The surgical clip according to claim 1, wherein a length of the protrusion in the longitudinal direction is the width of the longitudinal groove in a transversal direction.

13. The surgical clip according to claim 1, wherein the center portion of one of the first clip branch and the second clip branch has a plane surface in the longitudinal direction and the opening/closing direction, and that plane surface faces the other of the first clip branch and the second clip branch.

14. A surgical clip of a branch-crossed design with a first clip branch and a second clip branch, respective center portions in a longitudinal direction of which each extend in a Z shape, which are connected to each other at respective proximal ends of the clip branches via a spring-elastic connection piece, and have, at respective distal portions of the clip branches, a jaw part with a gripping surface, wherein in a mounting position of the clip, the clip branches are crossed over, the gripping surfaces lie opposite each other, and are held lying against each other via a closing force of the spring-elastic connection piece, wherein at least the first clip branch has a longitudinal groove in its center portion, the longitudinal groove extending in a Z-shaped manner and open only towards the second clip branch, in which the second clip branch is supported and/or guided in its center portion extending in a Z-shaped manner, at least in sections of the second clip branch, in such a way that a relative movement of the clip branches in an opening/closing direction along the longitudinal groove is possible, but a displacement of the clip branches in a direction transverse to the opening/closing direction is prevented, wherein a first side wall or a first flank of the longitudinal groove is a protrusion with an end face facing the second clip branch in the longitudinal direction so that the longitudinal groove is an open longitudinal groove, and a second side wall or a second flank of the longitudinal groove is formed by the center portion of the first clip branch, wherein the center portion of the second clip branch has a recess which is provided and adapted to guide and/or receive the protrusion arranged at the first clip branch, and wherein a length of the protrusion in the longitudinal direction is the width of the longitudinal groove in a transversal direction.

\* \* \* \* \*